(12) United States Patent
Leustek

(10) Patent No.: US 6,576,819 B1
(45) Date of Patent: Jun. 10, 2003

(54) METHODS FOR MODULATING THE LEVELS OF ORGANIC SULFUR COMPOUNDS IN PLANTS BY TRANSFORMING WITH (P)APS REDUCTASE DNA

(75) Inventor: Thomas Leustek, Union, NJ (US)

(73) Assignees: Pioneer Hi-Bred International, Inc., Des Moines, IA (US); Rutgers University, New Brunswick, NJ (US)

(*) Notice: Subject to any disclaimer, the term of this patent is extended or adjusted under 35 U.S.C. 154(b) by 0 days.

(21) Appl. No.: 09/252,319

(22) Filed: Feb. 18, 1999

(51) Int. Cl.$^7$ .............................. A01H 5/00; A01H 5/10; C12N 15/82
(52) U.S. Cl. ...................... 800/320; 800/278; 800/298; 435/419
(58) Field of Search ................................. 800/278, 298, 800/306, 312, 320, 320.1, 320.2; 435/419, 468, 69.1, 430; 536/23.2, 23.7, 23.1, 23.74

(56) References Cited

FOREIGN PATENT DOCUMENTS

| WO | WO 97/41239 | 11/1997 |
|---|---|---|
| WO | WO 00/04161 A1 | 1/2000 |
| WO | WO 00/36127 A1 | 6/2000 |
| WO | WO 01/75130 A1 | 10/2001 |

OTHER PUBLICATIONS

Maimann et al., Enhanced cystabhionine beta–lyase activity in transgenic potato plants does not force metabolite flow towards methionine, Dec. 2001, vol. 214, No.2, pp. 163–170.*
Genbank Accession No. Z69372, 1994.*
Genbank Accession No. U56921, 1998.*
Genbank Accession No. U25840, 1997.*
Genbank Accession No. AJ001223, 1998.*
Genbank Accession No. Z23169, 1996.*
Genbank Accession No. Y07525, 1991.*
Genbank Accession No. U53865, 1996.*
Korch, C. et al., Cloning, Nucleotide Sequence, and Regulation of MET14, the Gene Encoding the APS Kinase of *Saccharomyces Cerevisiae*, *Mol. Gen. Genet*, 1991, vol. 229, pp. 96–108.
Jain, A. et al., A cDNA Clone for 5'–Adenylylphosphosulfaten Kinase from *Arabidopsis Thaliana*, *Plant Physiol.*, 1994, vol. 105, pp. 771–772.
Kim, J. et al., Cloning and Analysis of the Gene for Cystathionine γ–Synthase from *Arabidopsis Thaliana*, *Plant Molecular Biology*, 1996, vol. 32, pp. 1117–1124, Klawer Academic Publishers, Belgum.
Brunold, C. et al., III. Regulation of Sulfur Metabolism in Plants: First Molecular Approaches, *Progress in Botany*, 1997, vol. 58, No. 58, pp. 164–186, Fortschritte Der Botanik, De Springer, Berlin.

Lee, S. et al., APS Kinase from *Arabidopsis Thaliana*: Genetic Organization, Expression, and Kinetic Analysis of the Recombinant Enzyme, *Biochemical and Biophysical Research Communications*, 1998, vol. 247, pp. 171–175, Article No. RC988751.
Bick, J. et al., Plant Sulfur Metabolism—The Reduction of Sulfate to Sulfite, *Current Opinion in Plant Biology*, Jun. 1998, vol. 1, No. 3, pp. 240–244, GB Quadrant Subscription Services.
Suter, M. et al., Adenosine 5'–Phasphosulfate Sulfotransferase and Adenosine 5'–Phosphosulfate Reductase Are Identical Enzymes, *The Journal of Biological Chemistry*, Jan. 14, 2000, vol. 275, No. 2, pp. 930–936.
Schwenn et al., Yeast PAPS Reductase: Properties and Requirements of the Purified Enzyme, ArchMicrobiol, 1988, 313–319, 150, Ruhr Universitat Bochum, Germany.
Krone et al., Characterisation of the Gene cysH and of its Product Phospho–adenylylsulphate reductase from *Escherichia coli*, Mol. Gen Genet, 1991, 314–319, 225,Ruhr University Bochum, Germany.
Gutierrez–Marcos et al., Three Members of a Novel Small Gene–Family from*Arabidopsis Thaliana* Able to Completement Functionally an*Escherichia Coli* Mutant Defective in PAPS Reductase Activity Encode Proteins With a Thioredoxin–Like Domain and "APS Reductase" Activity, Proc. Natl. Acad. Sci. USA, Nov. 1996, 13377–13382, 93, University of St. Andrews, United Kingdom.
Setya et al., Sulfate Reductioin In Higher Plants: Molecular Evidence for a Novel 5'–adenylylsulfate Reductase, Proc. Natl. Acad. Sci. USA, Nov. 1996, 13383–13388, 93, Rutgers University, New Brunswick, NJ.
Azevedo et al, The Biosynthesis and Metabolism of the Aspartate Derived Amino Acids in Higher Plants, Phytochemistry, 1997, 395–419, 46:3,Elsevier Science Ltd., Great Britain.

(List continued on next page.)

*Primary Examiner*—Amy J. Nelson
*Assistant Examiner*—Russell Kallis
(74) *Attorney, Agent, or Firm*—Alston & Bird LLP

(57) ABSTRACT

Methods for modulating levels of at least one organic sulfur compound in plants are provided. Also provided are plants, plant seeds, and plant cells produced by the methods. The methods comprise stably transforming a plant with a DNA construct encoding at least one APS reductase enzyme or PAPS reductase enzyme (herein, "(P)APS reductase") so that the transformed plant exhibits altered levels of at least one organic sulfur compound. APS reductase is an enzyme classified as EC 1.8.4.9 and PAPS reductase is an enzyme classified as EC 1.8.99.4; these enzymes are capable of reducing sulfur in the form of APS or PAPS to produce sulfite. Also provided are methods for reducing oxidative stress in plants and for increasing the nutritional quality of plants and seeds.

22 Claims, 1 Drawing Sheet

OTHER PUBLICATIONS

R. Hell, Molecular Physiology of Plant Sulfur Metabolism, Planta, 1997, 138–148, 202,Ruhr–Universität Bochum, Germany.

Bick et al., Glutaredoxiin Function for the Carboxyl–Terminal Domain of the Plant–Type 5' adenylylsulfate Reductase, Proc. Natl. Acad. Sci. USA, Jul. 1998, 8404–8409, 95, Rutgers University, New Brunswick, NJ and Harvard Medical School, Boston, MA.

Fujioka, M., "Mammalian Small Molecule Methyltransferases: Their Structural and Functional Features", *Int. J. of Biochem.*, 1992 pp. 1917–1924, vol. 24, Pergamon Press, Ltd., GB.

Gary, J. et al., "The Predominant Protein–arginine Methyltransferase from *Saccharomyces cerevisiae*,", *Journal of Biological Chemistry*, 1996, pp. 12585–12594, vol. 271(21), The American Society for Biochemistry and Molecular Biology, Inc., USA.

Giovanelli, J., et al., "Sulfer Amino Acids in Plants," *The Biochemistry of Plants*, 1980, pp. 453–505, vol. 5., Academic Press, USA.

James, F., et al., "Purification and Properties of S–Adenosyl-$_L$–methionine: $_L$Methionine S–Methyltransferase from *Wollenstonia biflora* Leaves," *The Journal of Biological Chemistry*, 1995, pp. 22344–22350, vol. 270(38), The American Society for Biochemistry and Molecular Biology, Inc., USA.

Joshi, C. and Chiang, V., "Conserved Sequence Motifs in Plant S–adenosyl–L–methionine–Dependent methyltransferases," *Plant Molecular Biology*, 1998, pp. 663–674, vol. 37(4), Kluwer Academic Publishers, Belgium.

Kagan, R. and Clarke, S., "Widespread Occurence of Three Sequence Motifs in Diverse S–Adenosylmethionine–Dependent Methyltransferases Suggests a Common Structure for These Enzymes," *Archives of Biochemistry and Biophysics*, 1994, pp. 417–427, vol. 310(2), Academic Press, Inc., USA.

Mudd, S. and Datko, A., "The S–Methylmethionine Cycle in *Lemna paucicostata*," *Plant Physiol.*, 1990, pp. 623–630, vol. 93(2), The American Society of Plant Physiologists, USA.

Pimenta, M., et al., S–Adenosyl-$_L$–Methionine: $_L$–Methionine S–Methyltransferase from Germinating Barley, *Plant Physiol.*, 1998, pp. 431–438, vol. 118.

Trossat, C., et al., "Salinity Promotes Accumulation of 3–Dimethylsulfoniopropionate and Its Precursor S–Methylmethionine in Chloroplasts," Plant Physiol., 1998, pp. 165–171, vol. 116.

* cited by examiner

METHODS FOR MODULATING THE LEVELS OF ORGANIC SULFUR COMPOUNDS IN PLANTS BY TRANSFORMING WITH (P)APS REDUCTASE DNA

FIELD OF THE INVENTION

The invention relates to the genetic manipulation of plants, particularly to altering sulfur metabolism in plants and plant seeds.

BACKGROUND OF THE INVENTION

Sulfur in its reduced form plays an important role in plant metabolism, being involved in the biosynthesis of a wide range of primary and secondary S-containing metabolites. In plants, sulfur metabolism includes the uptake of sulfate from the environment, assimilation into organic compounds, and channeling into proteins and secondary substances.

Plants and microorganisms are able to reduce sulfate to sulfide for synthesis of the thiol group of cysteine. Sulfate is first activated by ATP sulfurylase, forming 5'-adenylylsulfate (APS). APS can be phosphorylated by APS kinase, forming 3'-phosphoadenosine-5'-phosphosulfate (PAPS). Either APS or PAPS can be used for sulfate reduction. Generally, prokaryotes and fungi use PAPS, whereas photosynthetic eukaryotes use APS.

Cysteine, methionine, and sulfur-containing vitamins such as biotin or thiamine are essential in human nutrition. Sulfur-mediated functions include electron transport in Fe/S-clusters, structural and regulatory roles via protein disulfide bridges, and catalytic centers. Additionally, secondary sulfur compounds include signaling molecules, anticarcinogens and atmospheric compounds. See Hell (1997) *Planta* 202:138.

Often plant protein is deficient in the sulfur amino acids, especially methionine, as well as other essential amino acids such as lysine and tryptophan. As a result, diets must be supplemented with these amino acids in order to provide a balanced diet. A goal of plant breeding has been to increase the amount of sulfur amino acids present in the seed.

A number of methods have been described for increasing sulfur amino acid content of plants. Generally, these methods provide for the overexpression of a high methionine seed storage protein. The method entails overexpressing the seed storage protein in a transformed plant. Previously, methods for increasing the sulfur amino acid content of crops were attempted through breeding. However, these methods have met with limited success. There is therefore a need for methods of producing significant levels of the sulfur amino acids in plants and plant seeds.

Aerobic organisms are vulnerable to damage from reactive oxygen species. This is a particular problem for plants because reactive oxygen species are generated as a byproduct of oxygenic photosynthesis and carbon dioxide fixation. It would therefore be desirable to provide a method for reducing oxidative stress in plants and for increasing the nutritional quality of plants and seeds.

SUMMARY OF THE INVENTION

An object of the present invention is to provide methods for increasing the nutritional value of plants.

Another object of the present invention is to provide plants and plant parts having increased nutritional value.

Another object of the present invention is to provide plants and plant parts having increased levels of organic sulfur compounds.

Another object of the present invention is to provide plants and plant parts having increased levels of methionine.

Another object of the present invention is to provide a method for decreasing oxidative stress in plants.

In accordance with the present invention, methods for modulating the level of at least one organic sulfur compound in plants are provided. Also provided are plants, plant tissues, plant seeds and plant cells produced by the methods. The methods comprise stably transforming a plant with a DNA construct encoding a (P)APS reductase enzyme. (P)APS reductase is defined as an enzyme that is capable of reducing sulfur in the form of APS or PAPS to produce sulfite. The (P)APS reductase) enzyme has an activity such that, the transformed plant exhibits altered levels of at least one organic sulfur compound. Also provided is a method for reducing oxidative stress in plants.

DETAILED DESCRIPTION OF THE INVENTION

Figure 1:
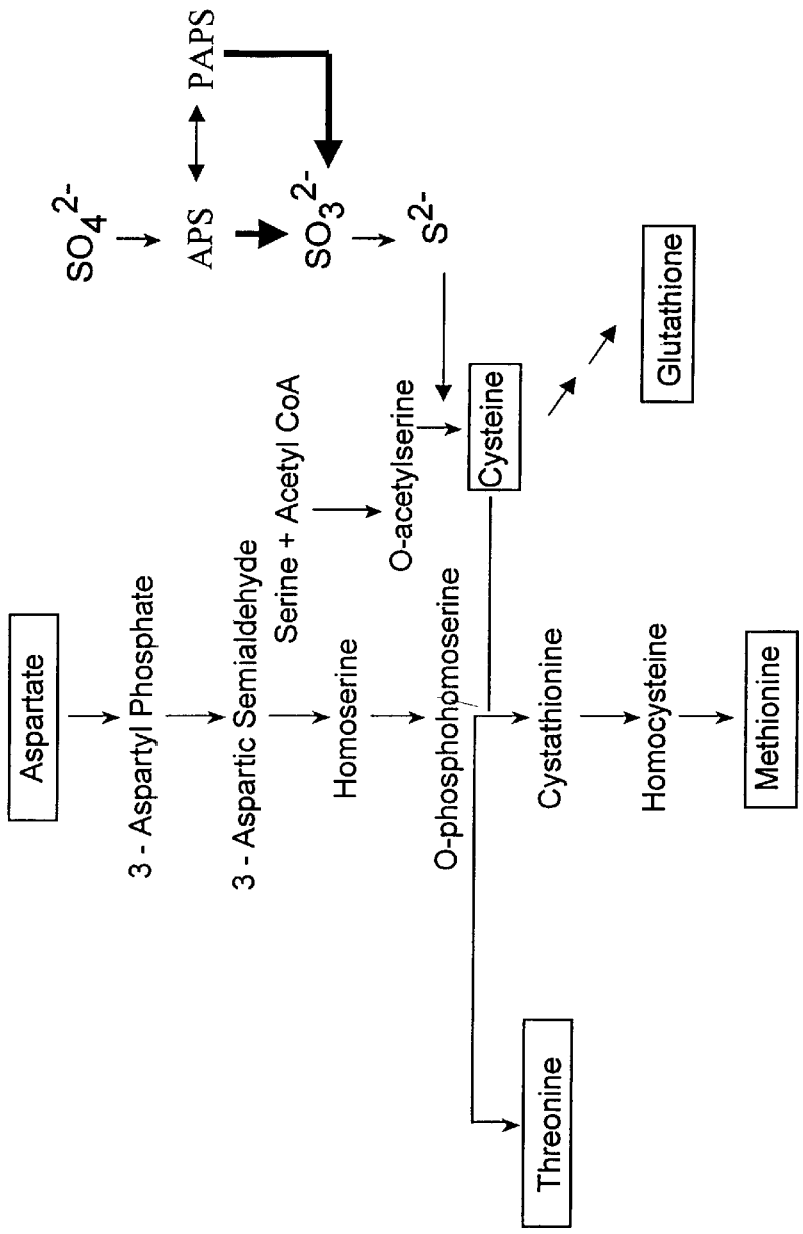
FIG. 1 sets forth the biosynthesis for the organic sulfur compounds cysteine and methionine with the proposed modifications of the invention.

In accordance with the subject invention, compositions and methods for modulating the biosynthesis of organic sulfur compounds in plants, particularly sulfur amino acids, more particularly cysteine and methionine are provided. The methods involve transforming a plant with one or more nucleic acid(s) encoding a (P)APS reductase enzyme capable of modulating the biosynthesis of at least one organic sulfur compound. The plant may also comprise one or more additional nucleic acid(s) selected from nucleic acids encoding enzymes involved in amino acid biosynthesis and sulfate reduction (FIG. 1).

By "organic sulfur compounds" is intended compounds such as glutathione, phytochelatins, sulfur-containing vitamins, glucosinolates, dimethylsulfoniopoprinate and amino acids such as methionine and cysteine.

APS reductase catalyzes a key reaction in the sulfate assimilation pathway of higher plants leading to the synthesis of cysteine and the antioxidant compound glutathione. In vitro biochemical studies revealed that the enzyme is activated by oxidation. Exposure of plants to ozone induces a rapid increase in APS reductase activity that coincides with the accumulation of cysteine and glutathione. These results indicate that redox regulation of APS reductase may provide a mechanism for rapid response to oxidative stress.

Glutathione is a tripeptide composed of the amino acids glutamate, cysteine and glycine. Glutathione exists in the reduced form and in the oxidized form which together form a biological redox buffer that is predominantly in a reduced state.

Sulfate reduction occurs in both roots and shoots of plants. Most of the sulfur transported in the xylem to the leaves is in non-reduced $SO_4^{2-}$. Some transport back to roots and other parts of the plant occurs through phloem, and both free $SO_4^{2-}$ and organic sulfur compounds are transported. In leaves, the process of sulfate reduction occurs in chloroplasts. In roots, most or all of the process occurs in proplastids.

The first step of sulfate assimilation in all cells is reaction of $SO_4^{2-}$ with ATP producing adenosine-5'-phosphosulfate (APS) and pyrophosphate. This step is catalyzed by ATP sulfurylase. In plants the sulfur of APS is further reduced by (P)APS reductase activity. This enzyme is markedly stimulated during oxidative stress and is a key enzyme in sulfate assimilation in plants. Under oxidative stress, the enzyme is stimulated about 40-fold. This change in activity appears to be related to a conformational change in the enzyme in response to a change in the redox status of the chloroplast.

Therefore, a preferred embodiment of the present invention is to provide (P)APS reductase expression, which is relatively active under reducing conditions, such as in the chloroplast. Other methods can be used for increasing the activity of the (P)APS reductase enzyme, such as protein engineering or DNA shuffling.

Glutathione biosynthesis is also activated under oxidative stress, as a mechanism to mitigate the effects of the stress. Thus, under conditions of oxidative stress, sulfate reduction is enhanced through the increased activity of (P)APS reductase enzyme. The flow of the resulting reduced inorganic sulfur is directed toward glutathione biosynthesis via cysteine by increased activity of glutathione biosynthetic enzymes.

ATP sulfurylase, the first enzyme in sulfate reduction, is relatively unresponsive to oxidative stress. Therefore, this enzyme does not represent a significant limiting factor in sulfate reduction, when sulfate itself is not limiting. Thus, as shown in FIG. 1, by supplying the chloroplast with a (P)APS reductase enzyme, which is metabolically active under reducing conditions, sulfate reduction and subsequently the production of organic sulfur compounds can be increased in the plant.

Other nucleic acids encoding enzymes involved in sulfate reduction or organic sulfur compound biosynthesis, such as cysteine and methionine biosynthesis, can be utilized to shunt the pathway in particular directions. For example, APS kinase can be utilized to shunt APS into PAPS, leading to additional substrate for (P)APS reductase enzyme. In the same manner, cystathionine gamma synthase can be utilized to direct the flow of cysteine toward methionine.

Also, antisense constructs for any of the enzymes can be utilized to direct biosynthesis into a particular product or to stop biosynthesis for the build-up of a particular compound. For example, an antisense construct for gamma glutamylsynthetase (gs) can be used to shunt reduced sulfur into methionine production from cysteine even under oxidative conditions.

Yeast and bacterial (P)APS reductase enzymes are relatively active under reducing conditions, whereas higher plant (P)APS reductase enzyme is relatively inactive under these conditions. Thus, the expression of bacteria or yeast or a modified (P)APS reductase enzyme in the chloroplast, which maintains a relatively reducing environment under normal conditions, is one method for enhancing sulfate reduction. In this manner, the metabolic pathway of interest can be manipulated for the high production of sulfur-containing amino acids or other downstream organic sulfur compounds.

As noted above, the pathway can also be manipulated to decrease levels of a particular compound by transformation of antisense DNA sequences that prevent the conversion of the precursor compound into the particular compound being regulated. This method can be useful for "shunting" reduced sulfur from one pathway to another.

Any means for producing a plant comprising the (P)APS reductase nucleic acid or both the (P)APS reductase nucleic acid and at least a second nucleic acid are encompassed by the present invention. For example, the second (or additional) nucleic acid(s) of interest can be used to transform a plant at the same time as the (P)APS reductase nucleic acid (cotransformation). The second nucleic acid can also be introduced into a plant that has already been transformed with the (P)APS reductase nucleic acid. Alternatively, transformed plants, one expressing the (P)APS reductase enzyme and one expressing the second nucleic acid, can be crossed to bring the nucleic acids together in the same plant. Subsequent crosses or transformations can bring additional sequences together in the plant.

Enzymes involved in cysteine and methionine biosynthesis are known in the art. See, for example, aspartokinase (Masakazu et al. (1992) "Mutant Aspartokinase Gene," Japan Patent 1994062866-A 1 Mar. 8, 1994, Accession No. E06825; Omori et al. (1993) *J. Bacteriol.* 175(3):785–794; Accession No. X60821; Moriya et al. (1995) Japan Patent 1997070291-A 13 Mar. 18, 1997; Accession No. E12770); aspartate semialdehyde dehydrogenase (Calzada, F. R. A., Direct Submission, Centro Nacional de Investigaciones Cientificas, Avenida 25 esq. 158 reparto Cubanacan, Playa Ciudad de la Habana, Codigo Postal 6990, CUBA (1997), Accession No. Y15281; Daniel et al. (1993) *J. Mol. Biol.* 232 (2):468–483; Accession No. Z22554; Chen et al. (1993) *J. Biol. Chem.*; Accession No. Z22554; Accession No. U90239; Brakhage et al. (1990) *Biochimie* 72(10):725–734; Accession No. Z75208; Gothel et al. (1997) *Eur. J. Biochem.* 244 (1):59–65; Accession No. Z75208); homoserine kinase (See number two under aspartokinase, Accession No. X60821; Nakabachi et al. (1997) *Insect Biochem. Mol. Biol.* 27:1057–1062; Accession No. AB004856; Ryoichi et al. (1986) Japan Patent 1987232392-A 1 Oct. 12, 1987 (JP 1986076298); Accession No. E01358; Sadao et al. Japan Patent 1993207886-A 4 Aug. 20, 1993; Accession No. D14072); threonine synthase (see number two under aspartokinase, Accession No. X6082; Accession No. Z46263; Rognes, S. E., Direct Submission, Oct. 24, 1994, to University of Oslo, Department of Biology, Blindern, 0316 Norway, Accession No. Z46263; Accession No. L41666; Clepet et al. (1992) *Mol. Microbiol.* 6(21):3109–3119; Accession No. X65033 S50569; Cami, B., Direct Submission, Mar. 11, 1992, Laboratoire de Chimie Bacterienne, Centre Nationale de la Recherche, Scientifique, 31 Chemin 1. Aiguier, BP 71 13277 Marseille Cedex, FRANCE, Accession No. X65033 S50569); cystathionine gamma synthase (cgs) (Kim and Leustek (1996) "Cloning and analysis of the gene for cystathionine gamma-synthase from *Arabidopsis thaliana*," Plant Mol. Biol. 32 (6), 1117–1124, USA, Accession No. AF069317; Locke et al., Direct Submission, Jun. 3, 1997, AG Biotechnology, Dupont AF Products, PO Box 80402, Wilmington, Del. 19880–0402 USA, Accession No. AF007786); cystathionine beta lyase (Bork et al. (1997) *Plant Physiol.* 115:864–864; Accession No. AJ001148; Sienko, M., Direct Submission, Jun. 5, 1995, Marzena Sienko, Genetics, Institute of Biochemistry and Biophysics, Pawinskiego 5a, Warsaw 02-106, POLAND, Accession No. U28383; Ravanel et al. (1995) *Plant Mol. Biol.* 29 (4):875–882; Accession No. L40511); methionine synthase (Kurvari et al. (1995) *Plant Mol. Biol.* 29:1235–1252; Accession No. U36197; Ravanel et al. (1998) *Proc. Natl. Acad. Sci. USA* 95(13):7805–7812; Accession No. U97200; Michalowski et al., Direct Submission, Jan. 12, 1997, Biochemistry, University of Arizona, BioSciences West 513, Tucson, Ariz. 85721 USA, Accession No. U84889; Eichel et al. (1995) *Eur. J. Biochem.* 230 (3):1053–1058; Accession No. X83499); ATP sulfurylase (Murillo et al. (1995) *Arch. Biochem. Biophys.* 323(1): 195–204; Accession No. U06275; Leustek et al. (1994) Plant Physiol. 105:897–902; Accession No. U05218; Bolchi et al., Direct Submission, Jul. 28, 1997, Scienze Biochimiche, Viale delle Scienze, Parma, PR 43100 ITALY, Accession No. AF016305; Laue et al. (1994) *J. Bacteriol.* 176:3723–3729; Accession No. L26897; Laeremans et al. Accession No. AJ001223); APS kinase (apk) (Korch et al. (1991) *Mol. Gen. Genet.* 229(1):96–108; Accession No. S55315; Arz etal. (1994) *Biochim. Biophys.* Acta 1218 (3):447–452; Accession No. AF044285; Schiffinann et al. "Isolation of cDNA clones encoding adenosine-5'-phophosulfate-kinase (EC2.7.1.25) from *Catharanthus roseus* (Accession No. AF044285) and an isoform (akn2) from *Arabidopsis* (Accession No. AF04335 1)(PGR98–1 16)," *Plant Physiol.* 117 (3): 1125 (1998); Accession No. AF044285; Jain et al. (1994) *Plant Physiol.* 105:771–772; Accession No. U05238; Lee et al. (1998) *Biochem. Biophys. Res. Commun.* 247:171175; Accession No. U05238); APS reductase (Speich et al. (1994) *Microbiology* 140 (Pt6):1273–1284; Accession No. Z69372; Setya et al. (1996) *Proc. Natl. Acad. Sci. USA* 93(23):13383–1338; Accession No. U56921; Bick et al. (1998) *Proc. Natl. Acad. Sci. USA* 95(14):8404–8409; Accession No. U56921); PAPS reductase (Krone et al. (1991) *Mol. Gen. Genet.* 225(2):314–319; Accession No. Y07525; Krone et al. (1990) FEBS Lett. 260 (1):6–9; Accession No. Y07525; Gutierrez-Marcos et al. (1996) *Proc. Natl. Acad Sci. USA* 93:13377–13382; Accession No. U53865; Schwenn, J. D., Direct Submission, Jul. 2, 1993, Ruhr-University-Bochum, Fac. Biology, Biochemistry of Plants, Universitaetsstr. 150, D44780 Bochum, GERMANY, Accession No. Z23169; see number five under ATP sulfurylase, Accession No. AJ001223; Bussey et al. (1997) *Nature* 387 (6632 Suppl.):103–105; Accession No. U25840 U00094); sulfite reductase (Accession No. Y07525; Accession No. Z23169; Hipp et al. (1997) *Microbiology* 143 (Pt 9):2891–2902; Accession No. U84760; Pott et al. (1998) *Microbiology* 144 (Pt 7):1881–1894; Accession No. U84760; Bork et al. (1998) *Gene* 212 (1):147–153; Accession No. Y10157; Mbeguie-A-Mbeguie et al. Accession No. AF071890; Bruehl et al. (1996) *Biochim. Biophys. Acta* 1295:119–124; Accession No. Z49217; Hummerjohann el al. (1998) *Microbiology* 144 (Pt 5):1375–1386; Accession No. AF026066; serine acetyltransferase (Accession No. X80938; Accession No. D88529; Saito et al. (1995) *J. Biol. Chem.* 270 (27):16321–16326; Accession No. D49535); cysteine synthase (Hesse et al. (1998) "Isolation of cDNAs encoding cytosolic (Accession No. AF044172) and plastidic (Accession No. AF044173) cysteine synthase isoforms from *Solanum tuberosum* (PGR98–057)," *Plant Physiol.* 116:1604, Accession No. AF044173; Brander et al. (1995) Plant Physiol. 108:1748–1748; Accession No. X85803; Topczewski et al. (1997) *Curr. Genet.* 31 (4):348–356; Accession No. U19395); gamma glutamylcysteine synthase (Powles et al. (1996) *Microbiology* 142 (Pt 9):2543–2548; Accession No. U81808 L7593 1; Accession No. AL031018; EU *Arabidopsis* sequencing project, Direct Submission, Jul. 3, 1998, at the Max-Planck-Institut fuer Biochemie, Am Klopferspitz 18a, D-82152 Martinsried, FRG, Accession No. AL031018); glutathione synthetase (Okumura et al. (1997) *Microbiology* 143 (Pt 9):2883–2890; Accession No. D88540; Inoue et al. (1998) *Biochim. Biophys. Acta* 1395 (3):315–320; Accession No. Y13804; Accession No. Y10984; Accession No. U22359).

Variants and functional fragments, including shufflents, of the above enzymes or of P(APS) reductase may also be utilized. It is only required that the enzymes have an activity sufficient to modulate the level of a particular organic sulfur compound in a plant. Variants can be produced by methods known in the art. Variant proteins include those proteins derived from the native protein by deletion (so-called truncation), addition, or substitution of one or more amino acids at one or more sites in the native protein.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad Sci. USA* 82:488–492; Kunkel et al. (1987) *Methods Enzymol.* 154:367–382; Sambrook et al. (1989) *Molecular Cloning: A Laboratory Manual* (2d ed., Cold Spring Harbor Laboratory Press, Plainview, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

The (P)APS reductase nucleic acids, as well as any additional genes of interest can be optimized for enhanced expression in plants of interest. See, for example, EPA0359472; W091/16432; Perlak et al. (1991) *Proc. Natl. Acad. Sci. USA* 88:3324–3328; and Murray et al. (1989) *Nucleic Acids Res.* 17:477–498. In this manner, the nucleic acids can be synthesized utilizing plant-preferred codons. See, for example, Murray et al. (1989) *Nucleic Acids Res.* 17:477–498, the disclosure of which is incorporated herein by reference. In this manner, synthetic nucleic acids can also be made based on the distribution of codons a particular host uses for a particular amino acid.

Another method for obtaining modified enzymes that can alter the level of at least one organic sulfur compound is by sequence shuffling. Sequence shuffling is described in PCT publication No. 96/19256. See also, Zhang et al. (1997) *Proc. Natl. Acad Sci. USA* 94:4504–4509. Libraries of recombinant polynucleotides are generated from a population of related sequence polynucleotides comprising sequence regions that have substantial sequence identity and can be homologously recombined in vitro or in vivo.

In some instances, the enzymes of interest are natively expressed in the plant. However, by transformation with heterologous promoters, expression levels or patterns can be altered. See, for example, Sambrook et al. (1989) *Molecular Cloning: A Laboratory Manual* (2d ed., Cold Spring Harbor Laboratory Press, Plainview, N.Y.) and Innis et al. (1990) PCR Protocols: *A Guide to Methods and Applications* (Academic Press, N.Y.).

In a preferred embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the nucleic acid of interest to the chloroplasts. Such transit peptides are known in the art. See, for example, Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romeretal. (1993) *Biochem. Biophys. Res. Commun.* 196:1414–1421; and, Shah et al. (1986) *Science* 233:478–481.

Chloroplast targeting sequences are known in the art and include the chloroplast small subunit of ribulose-1,5- bisphosphate carboxylase (Rubisco), (de Castro Silva Filho et al. (1996) *Plant Mol. Biol.* 30:769–780; Schnell et al. (1991) *J. Biol. Chem.* 266(5):3335–3342); 5-(enolpyruvyl) shikimate-3-phosphate synthase (EPSPS) (Archer et al. (1990) *J. Bioenerg. Biomemb.* 22(6):789–810); tryptophan synthase (Zhao et al. (1995) *J. Biol. Chem.* 270(11): 6081–6087); plastocyanin (Lawrence et al. (1997) *J. Biol. Chem.* 272(33):20357–20363); chorismate synthase (Schmidt et al. (1993) *J. Biol. Chem.* 268(36) :27477–27457); and the light harvesting chlorophyll alb binding protein (LHBP) (Lamppa et al. (1988) *J. Biol. Chem.* 263:14996–14999). See also Von Heijne etal. (1991) *Plant Mol. Biol. Rep.* 9:104126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and Shah et al. (1986) *Science* 233:478–481.

Methods for transformation of chloroplasts are known in the art. See, for example, Svab et al. (1990) *Proc. Natl. Acad. Sci. USA* 87:8526–8530; Svab and Maliga (1993) *Proc. Natl. Acad Sci. USA* 90:913–917; Svab and Maliga (1993) *EMBO J.* 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-specific expression of a nuclear-encoded and plastid-directed RNA polymerase. Such a system has been reported in McBride et al. (1994) *Proc. Natl. Acad. Sci. USA* 91:7301–7305.

The nucleic acids can be combined with constitutive, tissue-specific, or chloroplast promoters for expression of the metabolite of interest. Such constitutive promoters include, for example, the core promoter of the Rsyn7 (U.S. Pat. No. 6,072,050 and PCT International Publication No. W099/43838), the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et a. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. patent application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

"Seed-specific" promoters of the invention include embryo-specific promoters. Additionally, such promoters include globulin 1, cruciferin, napin, B-conglycinin, phaseolin, as well as other promoters associated with storage proteins or involved in fatty acid biosynthesis.

Expression cassettes will comprise a transcriptional initiation region linked to the coding sequence or antisense sequence of the nucleotide of interest. Such an expression cassette is generally provided with a plurality of restriction sites for insertion of the sequence to be under the transcriptional regulation of the regulatory regions. The expression cassette may additionally contain selectable marker genes.

The transcriptional initiation region, the promoter, may be native or analogous or foreign or heterologous to the plant host. Additionally, the promoter may be a synthetic sequence. By foreign is intended that the transcriptional initiation region is not found in the native plant into which the transcriptional initiation region is introduced.

The transcriptional cassette will include in the 5'-to-3'direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671674; Sanfacon et al. (1991) *Genes Dev.* 5:141–149; Mogen et al. (1990) *Plant Cell.* 5 2:1261–1272; Munroe et al. (1990) *Gene* 91:151–158; Ballas et al. (1989) *Nucleic Acids Res.* 17:7891–7903; Joshi et al. (1987) *Nucleic Acids Res.* 15:9627–9639.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Transformation protocols as well as protocols for introducing nucleotide sequences into plants may vary depending on the type of plant or plant cell, i.e. monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad Sci. USA* 83:5602–5606, Agrobacterium-mediated transformation (Townsend et al., U.S. Pat. No. 5,563,055); direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture. Fundamental Methods*, ed. Gamborg and Phillips (Springer-Verlag, Berlin); and McCabe et al. (1988) *Biotechnology* 6:923–926). Also see Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein el al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture. Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren and Hooykaas (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The biosynthesis of organic sulfur compounds can be altered in any plant of interest. Of particular interest are plants useful for human and domestic animal food. Such plants include forages and seed crop plants such as cereal crops and oil seed crops. Of particular interest are plants where the seed is produced in high amounts, or the seed or a seed part is edible. Seeds of interest include the oil seeds, such as seeds from Brassica, cotton, soybean, safflower, sunflower, coconut, palm, etc.; grain seeds such as wheat, barley, rice, corn, etc.; other seeds including oats, pumpkin, squash, poppy, sesame, peanut, peas, beans, cocoa, coffee, etc.; and tree nuts such as walnuts, pecans, almonds, etc. Especially preferred plants are corn, soybean, sunflower, Brassica, wheat, barley, rye, rice, millet, sorghum, safflower, potato, pea, and alfalfa.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The following examples are offered by way of illustration and not by way of limitation.

EXAMPLES

Example 1

Transformation and Regeneration of Maize Callus

Immature maize embryos from greenhouse donor plants are bombarded with a plasmid containing a (P)APS reductase nucleic acid operably linked to the ubiquitin promoter plus a plasmid containing the selectable marker gene PAT (Wohileben et al. (1988) *Gene* 70:25–37) that confers resistance to the herbicide Bialaphos. Transformation is performed as follows.

The ears are surface sterilized in 30% Clorox bleach plus 0.5% Micro detergent for 20 minutes, and then rinsed two times with sterile water. The immature embryos are excised and placed embryo axis side down (scutellum side up), 25 embryos per plate, on 560 Y medium for 4 hours and then aligned within the 2.5-cm target zone in preparation for bombardment.

A plasmid vector comprising a (P)APS reductase nucleic acid operably linked to the ubiquitin promoter is constructed. This plasmid DNA plus plasmid DNA containing a PAT selectable marker is precipitated onto 1.1 $\mu$m (average diameter) tungsten pellets using a $CaCl_2$ precipitation procedure as follows: 100 $\mu$l prepared tungsten particles in water, 10 $\mu$l (1 $\mu$g) DNA in TrisEDTA buffer (1 $\mu$g total), 100 $\mu$l 2.5 M $CaCl_2$ and 10 $\mu$l 0.1 M spermnidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium, an N6 based medium, for 2 days, then transferred to 560R selection medium, an N6 based medium containing 3 mg/liter Bialaphos, and subcultured every 2 weeks. After approximately weeks of selection, selection-resistant callus clones are sampled for PCR and activity of the nucleic acid of interest. Positive lines are transferred to 288J medium, an N6 based medium with lower sucrose and hormone levels, to initiate plant regeneration. Following somatic embryo maturation (2–4 weeks), well-developed somatic embryos are transferred to medium for germination and transferred to the lighted culture room. Approximately 7–10 days later, developing plantlets are transferred to medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored for expression of the (P)APS nucleic acid and methionine.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for altering the level of at least one sulfur amino acid or glutathione in plants, the method comprising stably transforming a plant with a DNA construct comprising a nucleic acid encoding a (P)APS reductase enzyme, wherein the nucleic acid is operably linked to a promoter that drives expression in a plant wherein the level of at least one sulfur amino acid or glutathione is altered.

2. The method of claim 1, wherein the construct further comprises a chloroplast transit peptide.

3. The method of claim 1, wherein the (P)APS reductase enzyme is a yeast (P)APS reductase enzyme.

4. The method of claim 1, wherein the (P)APS reductase enzyme is a bacterial (P)APS reductase enzyme.

5. The method of claim 1, wherein the amino acid is cysteine or methionine.

6. A plant having increased levels of at least one sulfur amino acid or glutathione, the plant having stably transformed into its genome a DNA construct comprising a nucleic acid encoding a (P)APS reductase enzyme, wherein the nucleic acid is operably linked to a promoter that drives expression in a plant.

7. The method of claim 1, wherein said (P)APS reductase enzyme is APS reductase.

8. The plant of claim 6, wherein the construct further comprises a chloroplast transit peptide.

9. The plant of claim 6, wherein the (P)APS reductase enzyme is a yeast PAPS reductase enzyme.

10. The plant of claim 6, wherein the (P)APS reductase enzyme is a bacterial PAPS reductase enzyme.

11. The plant of claim 6, wherein the amino acid is cysteine or methionine.

12. The plant of claim 6, wherein the plant is a monocot.

13. The plant of claim 12, wherein said monocot is selected from the group consisting of maize, wheat, barley, rye, rice, millet, and sorghum.

14. The plant of claim 6, wherein the plant is a dicot.

15. The plant of claim 14, wherein said dicot is selected from the group consisting of soybean, sunflower, Brassica, and alfalfa.

16. A transformed seed of the plant of claim 6.

17. A plant cell having increased levels of at least one sulfur amino acid or glutathione, the plant cell having stably transformed into its genome a DNA construct comprising a nucleic acid encoding a (P)APS reductase enzyme, wherein the nucleic acid is operably linked to a promoter that drives expression in a plant.

18. The plant cell of claim 17, wherein the construct further comprises a chloroplast transit peptide.

19. The plant cell of claim 17, wherein the (P)APS reductase enzyme is a yeast PAPS reductase enzyme.

20. The plant cell of claim 17, wherein the (P)APS reductase enzyme is a bacterial (P)APS reductase enzyme.

21. The plant of claim 6, wherein said (P)APS reductase enzyme is APS reductase.

22. The plant cell of claim 17, wherein said (P)APS reductase enzyme is APS reductase.

* * * * *

UNITED STATES PATENT AND TRADEMARK OFFICE
CERTIFICATE OF CORRECTION

PATENT NO. : 6,576,819 B1
DATED : June 10, 2003
INVENTOR(S) : Leustek et al.

It is certified that error appears in the above-identified patent and that said Letters Patent is hereby corrected as shown below:

<u>Title page,</u>
Item [75], Inventor, insert -- Mitchell C. Tarczynski, West Des Moines, IA (US) --.

Signed and Sealed this

Twenty-first Day of October, 2003

JAMES E. ROGAN
*Director of the United States Patent and Trademark Office*